United States Patent
Brenan et al.

[11] Patent Number: 6,088,100
[45] Date of Patent: Jul. 11, 2000

[54] THREE-DIMENSIONAL LIGHT ABSORPTION SPECTROSCOPIC IMAGING

[75] Inventors: Colin J. H. Brenan, Marblehead; Ian W. Hunter, Lincoln, both of Mass.

[73] Assignee: Massachusetts Institute of Technology, Cambridge, Mass.

[21] Appl. No.: 09/106,247

[22] Filed: Jun. 29, 1998

Related U.S. Application Data
[60] Provisional application No. 60/052,458, Jul. 14, 1997.

[51] Int. Cl.[7] .................................................... G01B 9/02
[52] U.S. Cl. .......................................... 356/346; 356/359
[58] Field of Search ..................................... 356/359, 360, 356/346

[56] References Cited

U.S. PATENT DOCUMENTS

| | | | |
|---|---|---|---|
| 3,753,619 | 8/1973 | Thorpe et al. | 356/346 |
| 5,377,003 | 12/1994 | Lewis et al. | 356/346 |
| 5,398,113 | 3/1995 | De Groot | 356/360 |
| 5,459,570 | 10/1995 | Swanson et al. | 356/345 |
| 5,465,147 | 11/1995 | Swanson | 356/360 |
| 5,491,552 | 2/1996 | Knüttel | 356/360 |
| 5,565,986 | 10/1996 | Knüttel | 356/346 |
| 5,610,716 | 3/1997 | Sorin et al. | 356/357 |

OTHER PUBLICATIONS

Chinn et al., "Optical coherence tomography using a frequency–turntable optical source", *Optics Letters*, vol. 22, No. 5, Mar. 1, 1997.

Swanson, "High–speed optical coherence domain reflectometry", *Optics Letters*, vol. 17, No. 2, Jan. 15, 1992.

Fukano et al., "Simultaneous measurment of thicknesses and refractive indices of multiple layers by a low–coherence confocal interfernce microscope", *Optics Letters*, vol. 21, No. 23, Dec. 1, 1996.

Tearney et al., "Determination of the refractive index of highly scattering human tissue by optical coherence tomography", *Optics Letters*, vol. 20, No. 21, Nov. 1, 1995.

Gayen et al., "Emerging Biomedical Imaging Techniques", *Optics & Photonics News*, Mar. 1996.

Clivaz et al., "High–resolution reflectometry in biological tissues", *Optics Letters*, vol. 17, No. 1, Jan. 1, 1992.

Huang et al., "Optical Coherence Tomography", *Science, Reports*, vol. 254, Nov. 22, 1991.

*Primary Examiner*—Robert H. Kim
*Attorney, Agent, or Firm*—Bromberg & Sunstein LLP

[57] ABSTRACT

An absorption imaging spectrometer for providing a three-dimensional spectral image of a light-transmitting sample. Temporally incoherent light is used to illuminate the sample, with a portion of the beam split off as a reference beam and subsequently recombined with the return beam from the sample after a variable delay path. An optical configuration is provided for modulating a time delay of the reference beam, with the interferogram obtained at each surface of dielectric discontinuity within the sample being deconvolved to derive an absorption spectrum.

8 Claims, 2 Drawing Sheets

THREE-DIMENSIONAL LIGHT ABSORPTION SPECTROSCOPIC IMAGING

The present application claims priority from U.S. provisional application Ser. No. 60/052,458, filed Jul. 14, 1997, which is herein incorporated by reference.

FIELD OF THE INVENTION

This invention relates to a method and apparatus for obtaining spectra of three-dimensional scenes, and more specifically, for obtaining spectra by means of optical coherence domain reflectometry in media which may be murky, including biological environments.

BACKGROUND ART

Non-destructive techniques for in situ analysis of samples whose chemical and compositional properties vary with position in three dimensions have many applications in the physical and biological sciences as well as in industrial process monitoring and quality control. In medical imaging, for example, 3-D spectrochemical images can be used for noninvasive in situ visualization, identification and discrimination between different types of healthy tissue and between healthy and diseased tissues. Clearly, this capability would be of great benefit to both patient and physician because it would aid in the rapid diagnosis of a potentially life threatening condition (e.g. benign versus cancerous tumors) in a manner less invasive than present biopsy techniques.

Analysis of spectra of materials throughout the electromagnetic spectrum, and, particularly in the optical and infrared portions of the spectrum, enables molecular species identification and provides information on molecular structure. Different parts of the spectrum are particularly suited to specific inquiries, as well known in the spectroscopic arts. For example, the structure of molecular rotation, molecular vibration, and electronic structure are typically characteristic of successively shorter spectroscopic regimes, from the far infrared to the visible. Other spectroscopic techniques, such as Raman scattering and fluorescence, wherein the wavelength of excitation differs from the wavelength of interrogation, are included within the understanding of "spectroscopy" in all instances used herein and in the appended claims.

Spectra of two-dimensional scenes are routinely obtained and analyzed. Several techniques are also known for acquiring three-dimensional (3-D) spectrochemical images. These include optical tomography, solution of the inverse photon scattering problem, confocal scanning optical microscopy, and deconvolution microscopy.

Optical tomography requires illumination of a body from a plurality of angles, with a camera moved in tandem with the source of illumination in order to record a series of 2-D images at different angular positions. Tomographic algorithms are then applied to the acquired data set to reconstruct a 3-D image of the illuminated volume. Optical tomography has been successful in 3-D reconstruction of visible light absorption and fluorescence images. The necessity to make many angularly-spaced optical transmission measurements on an isolate specimen makes this approach slow and prevents its usage where there is limited access to the specimen (such as inside the body).

In the inverse scattering approach, a consistent solution is sought to a series of spatially-resolved time or frequency domain measurements to recover the 3-D spectroscopic image. Mostly applicable to 3-D spectrochemical imaging through a highly scattering medium, this technique has been demonstrated with some success for acquisition of 3-D fluorescence and near infrared (NIR) absorption spectroscopic images. The drawbacks of this approach include the non-uniqueness and instability of the solutions obtained and the computational-intensivity of the technique.

A third approach utilizes the inherent spatial discrimination properties of the confocal scanning optical microscope (CSOM). The CSOM combines focused illumination with spatially filtered detection of the back (or forward) scattered optical wave to detect light that originates from a small volume element (voxel) within the sample and attenuate light from out-of-focus. Moving the sample relative to the voxel and recording either the absorption, fluorescence or Raman spectrum of light passed through the pinhole spatial filter enables construction of a 3-D spectrochemical image of the scanned sample volume.

A fourth option entails measuring the 3-D point spread function (PSF) characterizing a particular optical imaging system (such as a conventional optical microscope), recording a series of axially-spaced 2-D-spectroscopic images with the imaging system, and recovering the original 3-D object by numerical deconvolution of the PSF from the 3-D image stack. This approach has been applied to a variety of spectroscopic image modalities including fluorescence, Raman and absorption spectroscopies. This approach suffers from the well-known numerical limitations of present deconvolution routines.

SUMMARY OF THE INVENTION

In accordance with a preferred embodiment of the present invention, there is provided an absorption imaging spectrometer for providing a three-dimensional absorption spectral image of a light-transmitting sample. The spectrometer has a source of temporally incoherent light, an interference medium sensitive to the temporally incoherent light with an input and a beam splitter for dividing the temporally incoherent light into a measurement beam along a measurement path incident on the sample and a reference beam along a reference path. The spectrometer also has an optical configuration for modulating a time delay of the reference beam and an optical combining means for supplying the reference beam and a reflected component of the measurement beam to the input of the interference medium. Additionally, the spectrometer has a signal processor coupled to the interference medium for producing an interferogram as a function of the time delay of the reference beam and a controller for calculating the three-dimensional absorption spectral image of a sample on the basis of the interferogram.

In accordance with alternate embodiments of the invention, the interference medium may be a substantially square-law medium or a photodetector, and the optical configuration for modulating the time delay of the reference beam may be a scanning mirror. The temporally incoherent light may be visible light or infrared light. The spectrometer may also have a stage for varying the disposition of the sample with respect to the measurement beam.

In accordance with another aspect of the present invention in one of its embodiments, there is provided a method of providing a three-dimensional absorption spectral image of a sample. The method has the steps of:

a. providing a source of temporally incoherent light;
b. dividing the temporally incoherent light into a measurement beam along a measurement path incident on the sample and a reference beam along a reference path;
c. varying an optical delay in the reference path;

d. combining a component of the measurement beam reflected from the sample with the reference beam onto an interference medium;

e. producing an interferogram as a function of the time delay of the reference beam;

f. calculating the three-dimensional absorption spectral image of a sample on the basis of the interferogram.

BRIEF DESCRIPTION OF THE DRAWINGS

The invention will be more readily understood by reference to the following description, taken with the accompanying drawings, in which.

DETAILED DESCRIPTION OF SPECIFIC EMBODIMENTS

Methods described herein combine optical coherence domain reflectometry (OCDR) with NIR and/or visible light absorption spectroscopy to create a new class of 3-D spectro-chemical imaging device. As discussed above, visible light and NIR absorption spectroscopies are well-established optical spectroscopic techniques for spectrochemical analysis of materials. OCDR is a well-established technique for 3-D imaging of the surfaces of transparent or weakly scattering structures (e.g. optical structures within the eye). OCDR is, in essence, a gating technique, exploiting the fact that only coherent light will give rise to optical interference, so that if an incoherent light beam is split, with a portion of the beam reflected off a surface, the recombined beam will exhibit interference effects only if the two portions of the beam have traveled substantially identical distances. This allows the distance to the reflecting surface to be determined with great precision. The resolution of OCDR is governed by the coherence time $t_c$ of the illuminating beam and is equal to the distance $\Delta l_c = c\, t_c/n$ traveled by light within the sample during a coherence time of the beam, where c is the speed of light in vacuum, and n is the index of refraction of the sample.

Previous embodiments of OCDR instrumentation, however, fail to recognize and exploit the spectroscopic information encoded in the coherently detected signals which, as previously discussed, signify reflections from dielectric surface boundaries spaced along the axis of propagation of the incident beam. This capability is recognized in the present invention and is explained below.

Figure 1:
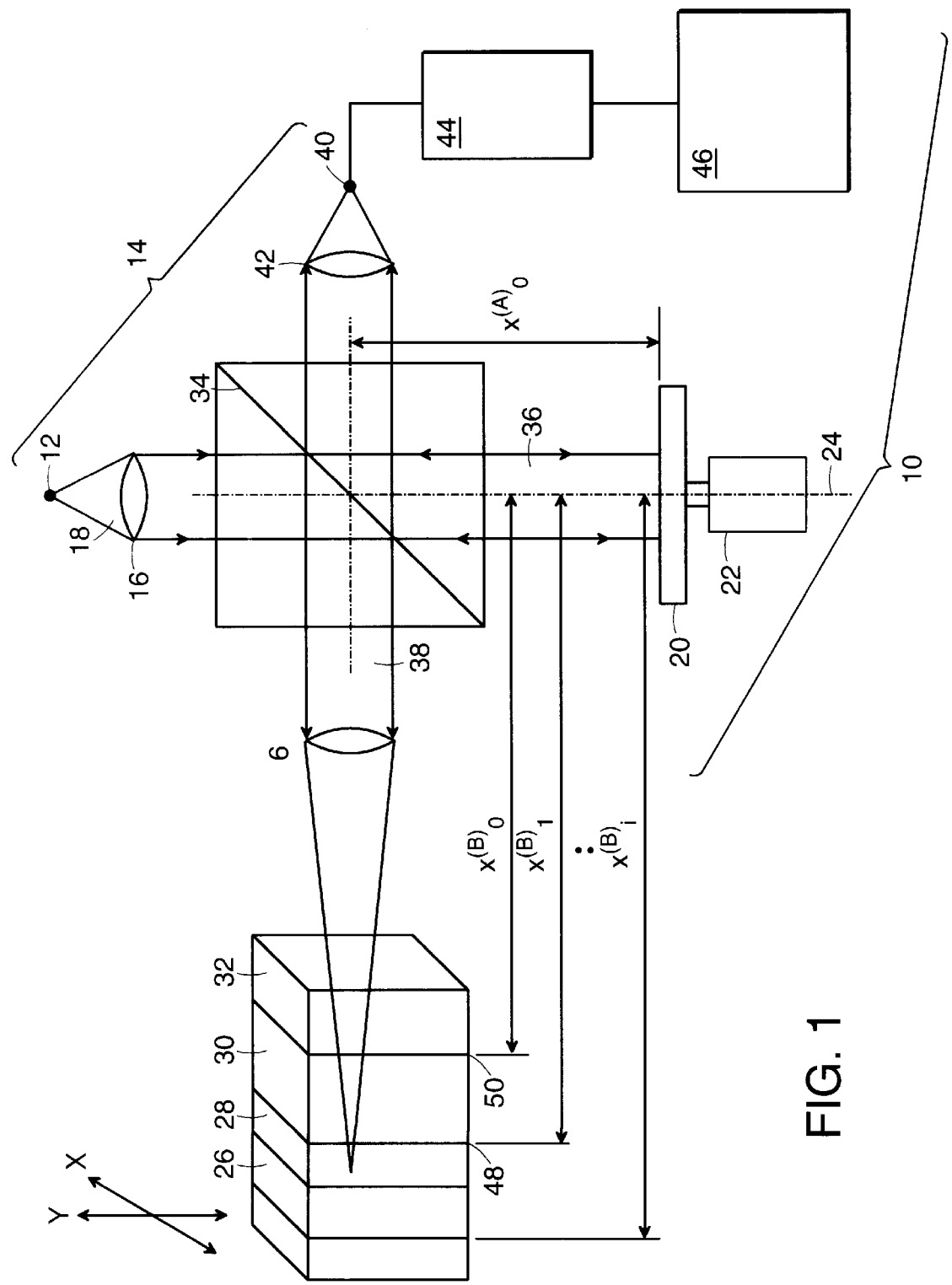
FIG. 1 is a schematic optical layout of a three-dimensional imaging spectrometer in accordance with a preferred embodiment of the present invention.

Referring to FIG. 1, an optical schematic is shown of an imaging spectrometer 10 in accordance with a preferred embodiment of the invention. Light from a temporally incoherent NIR and/or visible light source 12 illuminates a two-beam interferometer designated generally by numeral 14. Denoting the optical field amplitude of the source as U(t), incoherence implies that the autocorrelation $G(\tau) \equiv \langle U^*(t) U(t+\tau) \rangle$ is a very narrow function of $\tau$, where $\langle \rangle$ denotes a time average over at least one optical cycle. Thus, source 12 is spectrally very broad, since the coherence time $\tau_c$, which is essentially the temporal breadth of the autocorrelation function $G(\tau)$, is an inverse transform pair of the spectral width $\Delta v_c$ of the source, such that $\tau_c = 1/\Delta v_c$.

Two-beam interferometer 14, as shown, is a Michelson-type interferometer, although illumination through a convex lens 16 in order to collimate output beam 18 of source 12 gives rise to an interferometer generally classified as a Twyman-Green interferometer. Interferometer 14 may also be a polarizing interferometer, for example, within the scope of the invention, or similarly any other interferometer known to persons skilled in the optical arts. Describing interferometer 14 in terms of a Michelson or Twyman-Green interferometer, a first interferometer mirror 20 is a total reflector which may be mounted on a linear translation stage 22 for translating mirror 20 along axis 24 toward and away from source 12. A second interferometer mirror is a sample 26 to be spectroscopically imaged. For the purposes of the current description, sample 26 may be assumed to be composed of planar layers 28, 30, and 32, each of a different material and each having a refractive index $n_i$, a thickness $L_i$ and an absorption spectrum $A_i(v)$ that is characteristic of the material. Dielectric interfaces (or discontinuities) between planar layers 28, 30, and 32 are denoted 48 and 50. If absorption in the material of sample 26 is assumed to follow Beer's law, the loss in optical power at frequency $v$ after propagation through the $i^{th}$ layer is:

$$A_i(v) = \frac{S_i(v)}{S_0(v)} = e^{-\alpha_i(v) L_i},$$

where $S_0(v)$ is the input spectrum and $S_i(v)$ is the output power spectral density, respectively, at optical frequency $v$, $\alpha_i(v)$ is the absorption coefficient of the i-th layer as a function of frequency, and $L_i$ is the thickness of the layer indexed by index i.

Light from optical source 12 is divided by a beamsplitter 34 into two optical beams 36 and 38. In accordance with a preferred embodiment of the invention, beams 36 and 38 may be of substantially equal intensity, although this is not required for practice of the invention. Beam 36 may be designated herein by the superscript "A" while beam 38 may be designated herein by the superscript "B".

Beam 36 retro-reflects from mirror 20, re-enters beamsplitter 34, and is directed by reflection from beamsplitter 34 towards a photodetector 40. Beam 38 is focused into sample 26 with a focusing optic 42 which may, for example, be a convex transmissive optic, as shown. Beam 38 reflects from sample 26 and, after passage through lens 42, is combined with Beam 36 by beamsplitter 34 such as to optically interfere on exiting beamsplitter 34. Convex lens 42, or equivalent focussing optic, focuses the interference pattern onto photodetector 40. Photodetector 40 may be any square-law detector, providing a current proportional to the product of any incident optical field and the complex conjugate of the optical field, as known in the electro-optical arts. Photodetector 40 converts the fluctuations in optical beam intensity (as a result of the optical interference) into corresponding fluctuations in current. Standard electronics 44 are then used to amplify the current and convert it into a digital signal for input to processor 46. Once the signal is in processor 46, software algorithms written to execute the analysis technique discussed below analyze the acquired signals.

The optical field reflected from mirror 20 is denoted as $U_0^{(A)}$ and the time needed for optical wave 36 to travel the distance $x_0^{(A)}$ (the distance from beam splitter 34 to mirror 20 and return) is $t_0$. The optical field reflected from the i-th dielectric surface (or dielectric discontinuity) in the sample is denoted $U_i^{(B)}$ and the time needed for the $i^{th}$ optical wave to travel $x_i^{(B)}$ is denoted $t_i$. The optical delay, $\tau_{ij}$, is the difference in arrival time, $t_i-t_j$, between optical waves $U_i$ and $U_j$ at photodetector 40. Thus, for example, there is an optical delay between optical fields $U_i^{(B)}$ and $U_j^{(B)}$ reflected from the $i^{th}$ and $j^{th}$ surfaces in sample 26 because the optical fields travel different distances (designated $x_i^B$) and $x_j^{(B)}$, respectively) to interfere at photodetector 40. Note the convention employed herein whereby "x" denotes an optical distance that is smaller than the physical distance by a factor of $\int n^{-1}(l)dl$, where n(l) is the effective refractive index along the propagation path of the beam through sample 26. Similarly, a time delay may also be imparted between $U_0^{(A)}$ and any other optical beam reflected from sample 26, with the duration of the delay depending on the position of mirror 20 with respect to beam splitter 34. Equivalently, the arrival time of beam $U_0^{(A)}$ may be varied by any other means, such as the interposition of a material of specified refractive index, within the scope of the invention. In particular, the time delay between $U_0^{(A)}$ and $U_i^{(B)}$ equals $\tau_{0i}=(x_0^{(A)}-x_i^{(B)})/c$, where c is the speed of light in vacuum.

Absorption spectra, $A_i(v)$, from each layer i are found on measurement of the interference signal as a function of time delay between $U_0^{(A)}$ and the $U_i^{(B)}$ imposed by translation of mirror 40. In accordance with a preferred embodiment of the invention, each layer may be modeled as a linear filter of the input optical field which has a spectrum $S_0(v)$. The optical spectrum of the beam exiting a given layer may be considered the product of the absorption spectrum $A_i(v)$ and the spectrum of the input optical beam $S_i(v)$.

In the correlation-domain, a similar relationship exists between the autocorrelations of the input and output optical signals; namely, the autocorrelation of the optical beam output from a specified layer is the convolution between the layer optical impulse response function, $a_i(\tau)$, and the autocorrelation of the input optical beam. The correlation and spectral domains are related by the Fourier transform and therefore are equivalent approaches to mathematically describing the relationship between input to and output from a linear system, as well-known in the art of signal processing.

In an interferometer illuminating a purely reflective surface, measurement of the interference signal as a function of time delay imposed by translation of mirror 20 gives the autocorrelation of the optical beam illuminating the interferometer. In the present situation, the interferometer gives the cross-correlation between the reference optical wave $U_0^{(A)}$ reflected from mirror 20 and the optical waves $U_i^{(B)}$ reflected from different layer interfaces 48 and 50 in sample 26. To see this, consider the photocurrent i($\tau$) generated as a function of the position of mirror 20 or, equivalently, time delays between the optical wave reflected from the mirror and those optical waves from the sample:

$$i(\tau) = R_0 \left| U_0^{(A)} + \sum_{i=1}^{N} U_i^{(B)} \right|^2,$$

where $R_0$ is proportional to the photosensor responsivity (in Amperes/Watt) and the brackets < > denote time averaging over at least one optical cycle. Expanding the foregoing expression yields the individual contributions to the photocurrent:

$$i(\tau) = R_0\{\langle|U_0^{(A)}|^2\rangle + \langle|U_0^{(B)}|^2\rangle + \langle|U_1^{(B)}|^2\rangle + \langle|U_2^{(B)}|^2\rangle + \ldots +$$
$$[\langle U_0^{(A)} U_0^{(B)*}\rangle + \langle U_0^{(A)*} U_0^{(B)}\rangle] +$$
$$[\langle U_0^{(A)} U_1^{(B)*}\rangle + \langle U_0^{(A)*} U_1^{(B)}\rangle] + \ldots +$$
$$[\langle U_1^{(B)} U_2^{(B)*}\rangle + \langle U_1^{(B)*} U_2^{(B)}\rangle] +$$
$$[\langle U_1^{(B)} U_3^{(B)*}\rangle + \langle U_1^{(B)*} U_3^{(B)}\rangle] + \ldots\}.$$

Writing Equation 3 in terms of correlation functions $G_{ij}(v_{ij})$, $$G_{ij}(\tau) = \langle U_i^*(t) U_j(t+\tau_{ij})\rangle,$$

and recognizing that $G(\tau)$ is a real symmetric function and that $I_i = \langle |U_i|^2 \rangle$ is the time-averaged optical intensity of the $i^{th}$ optical wave incident on the photosensor results, the photocurrent as a function of delay, i.e., the interferogram, may be represented as:

$$i(\tau) = 2R_0\{I_0^{(A)} + I_0^{(B)} + I_1^{(B)} + I_2^{(B)} \ldots +$$
$$G_{00}(\tau_{00}) + G_{01}(\tau_{01}) + G_{02}(\tau_{02}) + G_{03}(\tau_{03}) + \ldots +$$
$$G_{12}(\tau_{12}) + G_{13}(\tau_{13}) + G_{14}(\tau_{14}) + G_{15}(\tau_{15}) + \ldots \}.$$

The interferogram recorded as a function of optical delay therefore contains several terms. As defined previously, the first set of term, $I_0^{(A)}$, $I_0^{(B)}$, $I_1^{(B)}$, . . . , are the time-averaged optical intensities of the light reflected from mirror 20 and sample 26. The second set of terms represent the interference between $U_0^{(A)}$ and the optical wave reflected from the in interface into sample 26. Indeed, the first term, $G_{00}(\tau_{00})$, is the optical autocorrelation of the optical source light spectrum $S_0(v)$ because it represents interference between $U_0^{(A)}$ and the front surface reflection $U_0^{(B)}$. The other terms in this group, $G_{0i}(\tau_{0i})$, represent the optical cross-correlation between $U_0^{(A)}$ and the other $U_i^{(B)}$ reflections from sample 26. The remaining terms of form $G_{ij}(\tau_{ij})$ are optical cross-correlations between waves reflected from different layers in sample 26.

The well-known Weiner-Khinchin theorem provides the necessary link between the measured optical correlation functions and the absorption spectra of each layer in the material. Simply put, the auto-correlation, $G_{ii}(\tau)$, and the auto-power spectral density $S_{ii}(v)$ are a Fourier transform pair:

$$S_{ii}(v) = \int_{-\infty}^{+\infty} G_{ii}(\tau) \exp(-j2\pi v\tau) d\tau.$$

Similarly, the cross-correlation, $G_{ij}(\tau)$, and the cross-power spectral density, $$S_{ij}(v) = \int_{-\infty}^{+\infty} G_{ij}(\tau) \exp(-j2\pi v\tau) d\tau$$

are also a Fourier transform pair. By taking the Fourier transform of each term in the expression for the photocurrent above, we can extract the auto-power spectrum of the optical source and cross-power spectrum equal to the absorption spectra of each layer through which the optical beam propagates. Specifically,

| | |
|---|---|
| input spectrum | $S_0(\nu)$ |
| $1^{st}$ layer | $S_1(\nu) = A_1(\nu)S_0(\nu)$ |
| $2^{d}$ layer | $S_2(\nu) = A_2(\nu)S_1(\nu) = A_2(\nu)A_1(\nu)S_0(\nu)$ |
| $\vdots$ | $\vdots$ |
| $i^{th}$ layer | $S_i(\nu) = A_i(\nu)S_{i-1}(\nu) = A_i(\nu) \ldots A_1(\nu)S_0(\nu)$. |

Absorption spectra for each layer are sequentially recovered from deconvolution (in either the time or frequency domain) of the optical correlation (or spectrum) measured for the $(i-1)^{th}$ layer from that measured for the in layer.

Separation of the interferograms corresponding to light reflected from each layer naturally results from the original requirement that the sample is illuminated with temporally incoherent and polychromatic light in the NIR/visible spectral region such as the light from a tungsten or xenon lamp. Since, as discussed above, the coherence time, $\tau_c$, and the spectral width of the optical source, $\Delta\nu_c$, are inverse transform pairs, $$\tau_c = \frac{1}{\Delta\nu_c},$$

thus for these optical sources with large spectral bandwidths, typically exceeding $\sim 10^{14}$ Hz, the coherence times can be less than $10^{-14}$ s. Given the speed of light ($c=3\times10^8$ m/s), this corresponds to a coherence length of less than 3 $\mu$m and thus surfaces within sample 26 may be resolved when separated by distances greater than this. Therefore, also, a distinct interferogram may be observed for $\tau_c$ less than one-half the round-trip time $c/n_iL_i$ through each layer.

This condition also guarantees that the cross-correlation terms $G_{ij}(\tau)$ are not observed. For example, one may consider the case of the electric field from the optical source having the form of a damped cosine, $$U(t) = A_0 e^{-\frac{1}{\tau_c}} e^{-j2\pi\nu t},$$

corresponding to a double-sided exponential autocorrelation function and a Lorentzian power-spectral density. Thus, $$G_{0i}(\tau_{0i}) = 2|A_0|^2 e^{-\frac{|\tau_{0i}|}{\tau_c}} \cos(2\pi\nu\tau_{0i})$$

in which $\tau_{0i}$ equals $|t_0-t_i|$, and $$G_{ij}(\tau_{ij}) = 2|A_0|^2 e^{-\frac{|\tau_{ij}|}{\tau_c}} \cos(2\pi\nu\tau_{ij})$$

where $\tau_{ij}$ equals $|t_i-t_j|$. $G_{ij}$ is therefore always zero for all i,j since $\tau_{ij} >> \tau_c$ is always true and $G_{0i}$ is zero only for $\tau_{0i} \geq \tau_c$; hence each $G_{0i}$ can be measured separately and the absorption spectrum of each layer can be found independently.

Figure 2:
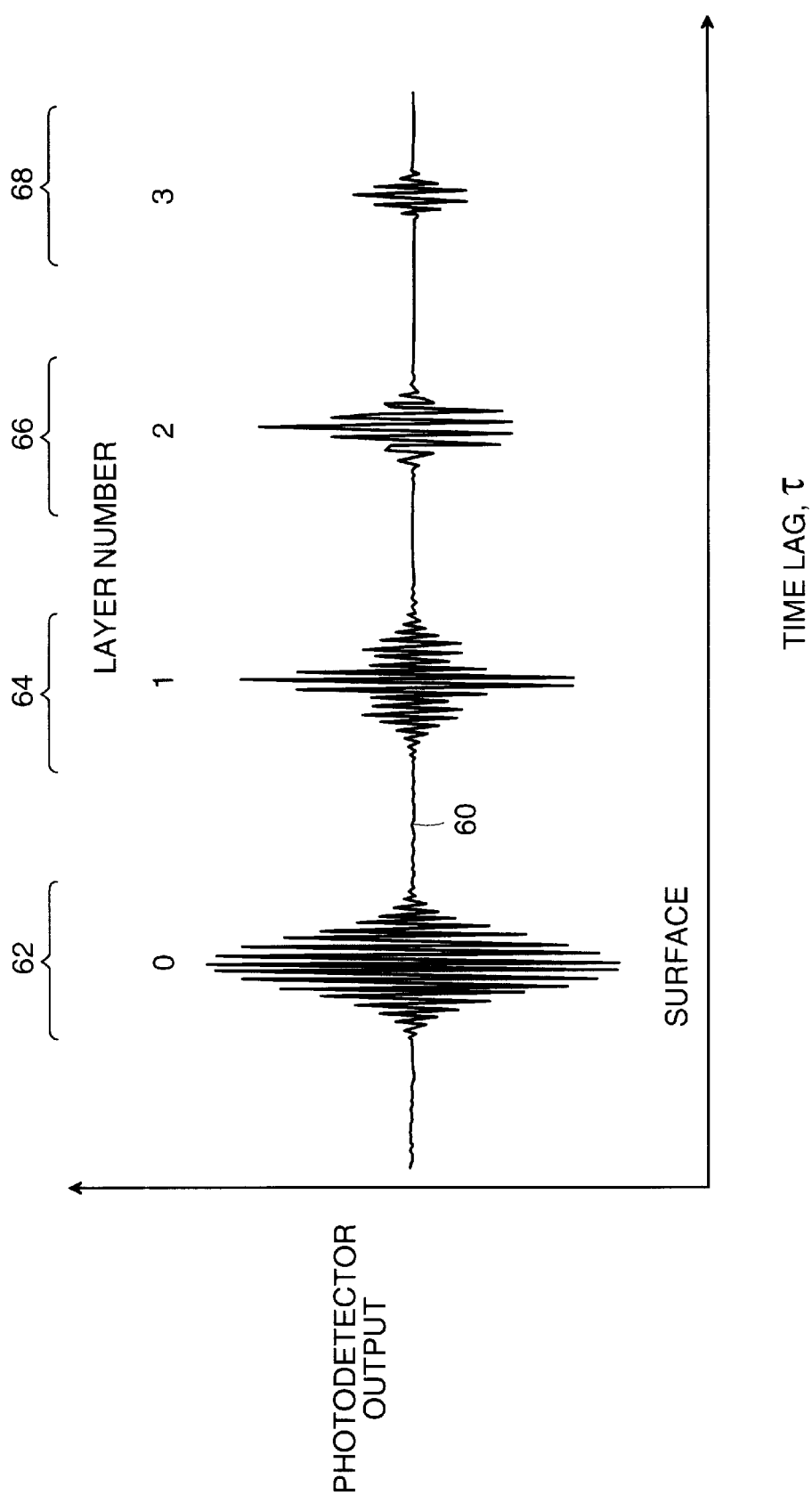
FIG. 2 is plot of interferogram response versus time in accordance with a preferred embodiment of the present invention, for the case of returns from a medium having discrete internal layers.

The sequence of events for acquisition of a 3-D absorption image in accordance with a preferred embodiment of the OCDR spectrometer begins by moving interferometer mirror 20 over a given distance, $x_i$, equal to the depth into the sample at which signal is to be detected. Referring now to FIG. 2, the resulting signal is recorded and stored in the computer, and, plotted as a function of time lag $\tau$, corresponds to interferogram 60. Interferogram 60 may be segmented into interferograms 62, 64, 66, and 68, corresponding to the reflections from the front surface and subsequent discrete boundaries within the sample. These interferograms are then stored in the computer with the mirror scan position equal to the point in the mirror scan at which each interferogram is a maximum. The $x_i$ position of the centroid of the first interferogram 62 is the zero reference position in the interferometer mirror scan and indicates the front surface of the sample. Subsequent positions of interferogram maxima in the interferometer mirror scan correspond to different depths into the sample.

The sample is then moved relative to the optical beam to a new XY position (where XY denotes the plane transverse to the propagation direction of the interrogating beam) by means, for example, of a motorized positioning unit (i.e. a stepping motor stage) and the procedure is repeated. After completion of the XY scan, each acquired interferogram is digitally Fourier transformed in the computer and the procedure as outlined above is applied to extract the absorption spectra from each region in the sample from which reflected light was detected. After this data analysis is complete the absorption spectra measured at each XY position in the sample are assembled and a 3-D spectrochemical image is generated based on, for example, the optical power in a given spectral channel as a function of 3-D position. Alternatively, changes in optical power in different spectral channels or some linear (or non-linear) combination of optical power in different spectral channels can be plotted for each XYZ position. The choice of processing and display algorithms to display specified information such as spectrochemical data is well known in the art of data reduction and presentation.

The described embodiments of the invention are intended to be merely exemplary and numerous variations and modifications will be apparent to those skilled in the art. All such variations and modifications are intended to be within the scope of the present invention as defined in the appended claims.

We claim:

1. An absorption imaging spectrometer for providing a three-dimensional absorption spectral image of a light-transmitting sample, the spectrometer comprising:

(a) a source of temporally incoherent light;

(b) an interference medium sensitive to the temporally incoherent light, the interference medium having an input;

(c) a beam splitter for dividing the temporally incoherent light into a measurement beam along a measurement path incident on the sample and a reference beam along a reference path;

(d) an optical configuration for modulating a time delay of the reference beam;

(e) an optical combining means for supplying the reference beam and a reflected component of the measurement beam to the input of the interference medium;

(f) a signal processor coupled to the interference medium for producing an interferogram as a function of the time delay of the reference beam;

(g) a controller for calculating the three-dimensional absorption spectral image of a sample on the basis of the interferogram.

2. A spectrometer according to claim 1, wherein the interference medium is a substantially square-law medium.

3. A spectrometer according to claim 1, wherein the interference medium is a photodetector.

4. An absorption imaging spectrometer according to claim 1, wherein the optical configuration for modulating the time delay of the reference beam is a scanning mirror.

5. An absorption imaging spectrometer according to claim 1, wherein the temporally incoherent light is visible light.

6. An absorption imaging spectrometer according to claim 1, wherein the temporally incoherent light is infrared light.

7. An absorption imaging spectrometer according to claim 1, further comprising a stage for varying the disposition of the sample with respect to the measurement beam.

8. A method of providing a three-dimensional absorption spectral image of a sample, the method comprising:

(a) providing a source of temporally incoherent light;

(b) dividing the temporally incoherent light into a measurement beam along a measurement path incident on the sample and a reference beam along a reference path;

(c) varying an optical delay in the reference path;

(d) combining a component of the measurement beam reflected from the sample with the reference beam onto an interference medium;

(e) producing an interferogram as a function of the time delay of the reference beam;

(f) calculating the three-dimensional absorption spectral image of a sample on the basis of theinterferogram.

* * * * *